United States Patent [19]
Smith, III et al.

[11] Patent Number: 6,080,414
[45] Date of Patent: Jun. 27, 2000

[54] LONG WEAR NAIL POLISH

[75] Inventors: Edward Dewey Smith, III, Mason; Peter Christopher Ellingson, Hamilton, both of Ohio; Michel Joseph Giret, Camberley; Stevan David Jones, Yateley, both of United Kingdom

[73] Assignee: The Proctor & Gamble Company, Cincinnati, Ohio

[21] Appl. No.: 09/071,097

[22] Filed: May 1, 1998

[51] Int. Cl.$^7$ .................................................. A61K 7/043
[52] U.S. Cl. ............................................ 424/401; 424/61
[58] Field of Search ...................... 424/401, 61

[56] References Cited

U.S. PATENT DOCUMENTS

| | | | |
|---|---|---|---|
| 4,277,380 | 7/1981 | Williams et al. | 260/18 |
| 4,384,058 | 5/1983 | Galante | 524/32 |
| 4,431,763 | 2/1984 | Reed | 524/389 |
| 4,442,259 | 4/1984 | Isgur et al. | 524/839 |
| 4,766,005 | 8/1988 | Montgomery et al. | 427/4 |
| 4,812,492 | 3/1989 | Eckes et al. | 523/351 |
| 4,844,102 | 7/1989 | Repensek et al. | 132/17 |
| 5,120,529 | 6/1992 | Koch et al. | 424/61 |
| 5,266,322 | 11/1993 | Myers et al. | 424/401 |
| 5,380,520 | 1/1995 | Dobbs | 424/61 |
| 5,538,717 | 7/1996 | La Poterie | 424/61 |
| 5,607,665 | 3/1997 | Calello et al. | 424/61 |
| 5,681,550 | 10/1997 | Rubino | 424/61 |
| 5,716,603 | 2/1998 | Chen et al. | 424/61 |
| 5,811,084 | 9/1998 | Busch, Jr. et al. | 424/61 |

FOREIGN PATENT DOCUMENTS

| | | |
|---|---|---|
| 87242557 | 8/1987 | Canada . |
| 0 022 452 A1 | 1/1981 | European Pat. Off. . |
| 0 061 348 A1 | 9/1982 | European Pat. Off. . |
| 0 063 467 A1 | 10/1982 | European Pat. Off. . |
| 0 325 038 A2 | 7/1989 | European Pat. Off. . |
| 0 418 469 A1 | 3/1991 | European Pat. Off. . |
| 0 455 373 A1 | 6/1991 | European Pat. Off. . |
| 0 627 212 | 5/1993 | European Pat. Off. . |
| 0 619 111 A1 | 12/1994 | European Pat. Off. . |
| 0299758 B1 | 12/1994 | European Pat. Off. . |
| 0 636 361 | 2/1995 | European Pat. Off. . |
| 0 637 600 A1 | 2/1995 | European Pat. Off. . |
| 0 658 609 A1 | 6/1995 | European Pat. Off. . |
| 0 679 384 | 11/1995 | European Pat. Off. . |
| 0 680 742 A1 | 11/1995 | European Pat. Off. . |
| 0 705 594 A1 | 4/1996 | European Pat. Off. . |
| 0 797 977 A1 | 10/1997 | European Pat. Off. . |
| 57-23632 | 2/1982 | Japan . |
| 4-03513 | 4/1992 | Japan . |
| 4-103512 | 4/1992 | Japan . |
| 5-148122 | 6/1993 | Japan . |
| 5-155737 | 6/1993 | Japan . |
| 5-310531 | 11/1993 | Japan . |
| 7-309721 | 11/1995 | Japan . |
| 4-103514 | 4/1996 | Japan . |
| 9-57135 | 6/1997 | Japan . |
| 9-268113 | 10/1997 | Japan . |
| 883078 | 11/1981 | U.S.S.R. . |
| WO 92/16185 | 3/1992 | WIPO . |
| WO 92/05762 | 4/1992 | WIPO . |
| WO 96/34061 | 10/1996 | WIPO . |
| WO 97/00664 | 1/1997 | WIPO . |
| WO 9742930 | 11/1997 | WIPO . |

OTHER PUBLICATIONS

U.S. application No. 09/070,960, Ellingson et al., filed May 1, 1998.
U.S. application No. 09/071,424, Ellingson et al., filed May 1, 1998.
U.S. application No. 09/071,098, Ellingson et al., filed May 1, 1998.
U.S. application No. 09/071,273, Ellingson et al., filed May 1, 1998.
U.S. application No. 09/071,423, Ellingson et al., filed May 1, 1998.
U.S. application No. 09/071,099, Ellingson et al., filed May 1, 1998.

*Primary Examiner*—Thurman K. Page
*Assistant Examiner*—S. Howard
*Attorney, Agent, or Firm*—Kelly L. McDow-Dunham; Loretta J. Henderson; David L. Suter

[57] ABSTRACT

The present invention relates to kits and films formed from the kits which are useful as cosmetic or therapeutic agents, as well as methods of their use. The films and kits herein are particularly useful as polishes for mammalian nails. More particularly, the present invention relates to kits and films which, when applied to mammalian nails exhibit long wear, particularly at the tip of the nail. When applied to mammalian nails, the present kits and films exhibit Tip Wear Indices, Total Wear Indices, and/or Jagged Indices of less than about 0.90. The present invention further relates to methods of coating mammalian nails with kits and films which exhibit Tip Wear Indices, Total Wear Indices, and/or Jagged Indices of less than about 0.90.

42 Claims, No Drawings

LONG WEAR NAIL POLISH

TECHNICAL FIELD

The present invention relates to kits useful as cosmetic or therapeutic agents and films formed from the kits having defined wear properties. The kits and films herein are particularly useful as polishes for mammalian nails.

BACKGROUND OF THE INVENTION

Consumers use nail polishes to cosmetically enhance their nails or protect the nails from everyday conditions and stressors. However, these nail polishes are deficient in many respects, including their inability to provide long wear. Nail polishes which are known or currently available often exhibit deterioration, particularly in the form of chipping or peeling, in as few as one or two days. Such deterioration is exhibited primarily at the tip of the nail. The occurrence of this deterioration often forces consumers to remove their nail polish soon after original application and reapply additional nail polish to the nails. Consumers may also attempt to correct the unsightly appearance of the deteriorating nail polish by "touching-up" the areas of the nail which exhibit the deterioration, a practice which actually impairs the overall look of the nail polish. Finally, consumers may choose to do nothing about the deterioration and allow, for example, chipping and peeling to progress, resulting in nails which are not only minimally protected from the environment but are unsightly as well.

The art is replete with nail polish compositions which are promoted as having long wear, good adhesion, and/or resistance to chipping. While some nail polish compositions provide better wear than others, a need remains for nail polishes which provide long wear.

Extreme examples of nail polish compositions which exhibit inadequate wear are those which are easily and completely peeled or stripped off the nails without the use of a solvent. See. e.g., EP 0,680,742, Mellul et al., assigned to L'Oreal.

Still further, other nail polish compositions are completely removable with water and, therefore, are not practical for normal use and do not provide long wear under everyday conditions. See. e.g., WP 05-155,737, Itsumi et al., assigned to Yuho Chemical Co. and EP 0,679,384, Ramin et al., assigned to L'Oreal.

It would therefore be desirable to provide nail polishes having improved wear properties. The present inventors have surprisingly discovered kits and films which, when applied to mammalian nails, exhibit long wear at a superior level not provided by the nail polishes which are presently known and used.

SUMMARY OF THE INVENTION

The present invention relates to kits and films formed from the kits which, when applied to mammalian nails, exhibit long wear. The present kits comprise two or more compositions, preferably a basecoat composition, a topcoat composition, and, optionally, a midcoat composition. Each composition comprises a film-forming polymer, a liquid diluent, and, optionally, other components. The present film-forming polymers are selected from polyurethanes, polyacryls, polymethacryls, cellulosic polymers, styrene-acryl copolymers, polystyrene-polyacryl mixtures, polysiloxanes, polyesters, urethane-acryl copolymers, siloxane-urethane copolymers, polyurethane-polymethacryl mixtures, silicone-acryl copolymers, vinyl acetate polymers, and mixtures thereof. When applied to mammalian nails, the present kits provide films exhibiting wear properties defined by a Total Wear Index of less than about 0.90, a Tip Wear Index of less than about 0.90, and/or a Jagged Index of less than about 0.90.

DETAILED DESCRIPTION OF THE INVENTION

The essential components of the present invention are herein described below. Also included are non-limiting descriptions of various optional and preferred components useful in the kits of the present invention.

The present invention can comprise, consist of, or consist essentially of any of the required or optional components and/or limitations described herein.

All percentages and ratios are calculated by weight unless otherwise indicated. All percentages are calculated based on the total composition unless otherwise indicated.

All component or composition levels are in reference to the active level of that component or composition, and are exclusive of impurities, for example, residual solvents or by-products, which may be present in commercially available sources.

Referred to herein are trade names for materials including, but not limited to, polymers and optional components. The inventors herein do not intend to be limited by materials under a certain trade name. Equivalent materials (e.g., those obtained from a different source under a different name or catalog (reference) number) to those referenced by trade name may be substituted and utilized in the kits, films, and methods herein.

All documents referred to herein, including all patents, patent applications, and printed publications, are hereby incorporated by reference in their entirety.

The kits and films of the present invention are suitable for use as a nail polish for mammalian nails. As used herein, the term "suitable for use as a nail polish for mammalian nails" means that the compositions, kits, or films thereof are suitable for use in contact with mammalian nails without undue toxicity, incompatibility, instability, allergic response, and the like.

As used herein, the term "nail polish" is a comprehensive term describing a nail polish composition, product (including coloring products), system, kit, or the like, which is usefull for providing, for example, aesthetic, therapeutic, or prophylactic benefits to the nail.

As used herein, the term "mammalian nail" means a keratinaceous plate present at the upper surface of the end of a finger or toe of a primate, most preferably a human, or the homologous claw or hoof of another mammal.

The layers and films herein may be joined to mammalian nails. As used herein, the terms "joined to", "joined to mammalian nails", or the like means in contact with or applied to a mammalian nail through physical forces in such a manner that the layer or film is contiguous to either the nail itself, a preceding layer, a succeeding layer, or matter previously applied to or existing on the nail. The layer or film may be "joined to" a mammalian nail, preceding layer, or succeeding layer even though other matter (such as another preceding or succeeding layer) intervenes. Accordingly, matter which is "joined to", for example, a mammalian nail, need not actually be contiguous to that mammalian nail.

As used herein, the term "contiguous to" means directly joined to by physical forces through touching and boundary sharing with essentially no intervening matter.

As used herein, the term "film" means one or more layers of a nail polish suitable for use on mammalian nails which forms when one or more compositions of the kit is applied to, and dries on, mammalian nails.

As used herein, the term "layer" means one substantially dry coat of nail polish which forms when a composition of the kit is applied to, and dries on, a mammalian nail.

As used herein, the term "preceding layer" means a layer which is joined to a nail and is closer in proximity to the nail as compared to a reference layer joined to the same nail. For example, wherein a basecoat and a topcoat are joined to a nail, the basecoat is a preceding layer relative to the topcoat. Similarly, wherein a basecoat, midcoat, and topcoat are joined to a nail, the basecoat and midcoat are preceding layers relative to the topcoat, and the basecoat is a preceding layer relative to both the midcoat and topcoat.

As used herein, the term "succeeding layer" means a layer which is joined to a nail and is further in proximity from the nail as compared to a reference layer joined to the same nail. For example, wherein a basecoat and a topcoat are joined to a nail, the topcoat is a succeeding layer relative to the basecoat. Similarly, wherein a basecoat, midcoat, and topcoat are joined to a nail, the midcoat and topcoat are succeeding layers relative to the basecoat, and the topcoat is a succeeding layer relative to both the basecoat and midcoat.

As used herein, the term "substantially dry" in reference to a film or a layer means that the film or layer feels dry, smooth, or not tacky when it is touched with a human fingertip.

Kits and Films of the Present Invention

The kits of the present invention, when applied to mammalian nails, provide films exhibiting long wear as defined by their Total Wear Index, Tip Wear Index and/or Jagged Index as defined herein. The kits comprise two or more compositions, preferably a basecoat composition, a topcoat composition, and, optionally, a midcoat composition. Each composition comprises a film-forming polymer, a liquid diluent, and, optionally, one or more other suitable components as described herein. As used herein, the term "film-forming polymer" means a homopolymer, copolymer, or mixture thereof which forms an adherent continuum from a composition when applied to mammalian nails. See, e.g., *Polymer Colloids*, Robert M. Fitch, ed., New York: Plenum Press, pp. 173–183 (1971). As used herein, the term "copolymer" includes linear, block, branched, graft, comb, and star copolymers.

Although the term "film-forming polymer" is used herein to describe a polymer in a composition, in some circumstances, polymerization may not actually take place until application of the composition (to the nail, for example) is performed. Accordingly, as used herein, the term "film-forming polymer" is meant to encompass monomers which have not yet polymerized but will upon application to the nail.

The film-forming polymers herein are preferably self-curing polymers. That is, the preferred polymers do not require chemical reaction or introduction of energy (e.g., exposure to ultraviolet rays) to form the adherent continuum.

The film-forming polymers herein can be selected from nonionic, ionic (anionic or cationic), and amphoteric (including zwitterionic) polymers. Wherein the film-forming polymer is water-borne, the polymer is preferably anionic.

The film-forming polymers herein are preferably, but are not limited to, solvent-borne or water-borne polymers. As used herein, the term "water-borne", with reference to a film-forming polymer, means that the polymer was prepared in a mixture comprising water and is preferably added to the composition which it comprises as a mixture (preferably a dispersion) in water. As used herein, the term "solvent-borne", with reference to a film-forming polymer, means that the polymer was prepared under substantially anhydrous conditions and is preferably added to the composition which it comprises as a substantially anhydrous mixture (preferably a solution).

Preferred film-forming polymers of the present invention are selected from polyurethanes, polyacryls, polymethacryls, cellulosic polymers, styrene-acryl copolymers, polystyrene-polyacryl mixtures, polysiloxanes, polyesters, urethane-acryl copolymers, siloxane-urethane copolymers, polyurethane-polymethacryl mixtures, silicone-acryl copolymers, vinyl acetate polymers, and mixtures thereof. The term "polyacryl" includes polyacrylates, polyacrylics, and polyacrylamides. The term "polymethacryl" includes polymethacrylates, polymethacrylics, and polymethacrylamides. The term "cellulosic polymers" includes all cellulose polymers, including esters thereof.

Examples of preferred polyacryls, polymethacryls, and styrene-acryl copolymers include Gelva® 2497 (commercially available from Monsanto Co., St. Louis, Mo.), Duraplus® 2 (commercially available from Rohm & Haas Co., Philadelphia, Pa.), Joncryl® 95 (commercially available from S.C. Johnson Polymer, Sturtevant, Wis.), SCX-1537 (S.C. Johnson Polymer), SCX-1959 (S.C. Johnson Polymer), SCX-1965 (S.C. Johnson Polymer), Joncryl® 530 (S.C. Johnson Polymer), Joncryl® 537 (S.C. Johnson Polymer), Glascol LS20 (commercially available from Allied Colloids, Suffolk, Va.), Glascol C37 (Allied Colloids), Glascol LS26 (Allied Colloids), Glascol LS24 (Allied Colloids), Glascol LE45 (Allied Colloids), Surcol 441® (Allied Colloids), Carboset® CR760 (commercially available from BFGoodrich, Cleveland, Ohio.), Carboset® CR761 (BFGoodrich), Carboset® CR763 (BFGoodrich), Carboset® 765 (BFGoodrich), Carboset® 19X2 (BFGoodrich), Carboset® XL28 (BFGoodrich), Hycar 26084 (BFGoodrich), Hycar 26091 (BFGoodrich), Carbobond 26373 (BFGoodrich), Neocryl® A-601 (commercially available from Zeneca Resins, Wilmington, Mass.), Neocryl® A-612 (Zeneca Resins), Neocryl® A-6044 (Zeneca Resins), Neocryl® A-622 (Zeneca Resins). Neocryl® A-623 (Zeneca Resins), Neocryl® A-634 (Zeneca Resins), and Neocryl® A-640 (Zeneca Resins).

An example of a preferred polysiloxane is PSA 590 (commercially available from General Electric, Waterford, N.Y.).

Examples of preferred urethane-acryl copolymers include Sancure® AU-4000 (commercially available from BFGoodrich), Sancure® AU-4010 (BFGoodrich), Witcobond A-100 (commercially available from Witco Performance Chemicals, Houston, Tex.), Witcobond W-610 (Witco Performance Chemicals), NeoPac R-9000 (commercially available from Zeneca Resins), NeoPac R-9030 (Zeneca Resins), and NeoPac R-9699 (Zeneca Resins).

Preferred polyurethanes are selected from aromatic polyether polyurethanes, aliphatic polyether polyurethanes, aromatic polyester polyurethanes, aliphatic polyester polyurethanes, aromatic polycaprolactam polyurethanes, and aliphatic polycaprolactam polyurethanes. The more preferred polyurethanes are selected from aromatic polyether polyurethanes, aliphatic polyether polyurethanes, aromatic polyester polyurethanes, and aliphatic polyester polyurethanes. Examples of preferred polyurethanes include Sancure 2710® and/or Avalure UR 445® (which are equivalent copolymers of polypropylene glycol, isophorone diisocyanate, and 2,2-dimethylolpropionic acid, having the International Nomenclature Cosmetic Ingredient name "PPG-17/PPG-34/IPDI/DMPA Copolymer"), Sancure 878®, Sancure 815®, Sancure 1301®, Sancure 2715®, Sancure 1828®, Sancure 2026®, Sancure 1818®, Sancure 853®, Sancure 830®, Sancure 825®, Sancure 776®, Sancure 850®, Sancure 12140®, Sancure 12619®, Sancure 835®, Sancure 843®, Sancure 898®, Sancure 899®, Sancure 1511®, Sancure 1514®, Sancure 1517®, Sancure 1591®, Sancure 2255®, Sancure 2260®, Sancure 2310®, Sancure 2725®, and Sancure 12471® (all of which are commercially available from BFGoodrich, Cleveland, Ohio.), Bayhydrol DLN (commercially available from Bayer Corp., McMurray, Pa.), Bayhydrol LS-2033 (Bayer Corp.), Bayhydrol 123 (Bayer Corp.), Bayhydrol PU402A (Bayer Corp.), Bayhydrol 110 (Bayer Corp.), Witcobond W-320 (commercially available from Witco Performance Chemicals), Witcobond W-242 (Witco Performance Chemicals), Witcobond W-160 (Witco Performance Chemicals), Witcobond W-612 (Witco Performance Chemicals), Witcobond W-506 (Witco Performance Chemicals), NeoRez R-940 (commercially available from Zeneca Resins), NeoRez R-960 (Zeneca Resins), NeoRez R-962 (Zeneca Resins), NeoRez R-966 (Zeneca Resins), NeoRez R-967 (Zeneca Resins), NeoRez R-972 (Zeneca Resins), NeoRez R-9409 (Zeneca Resins), NeoRez R-9637 (Zeneca), NeoRez R-9649 (Zeneca Resins), and NeoRez R-9679 (Zeneca Resins).

Preferred solvent-borne polyurethanes include Sanres EX499® (hexylene glycol/neopentyl glycol/isophorone diisocyanate copolymer, Sanres 1271 ®, Sanres 6010®, and Sanres 6012® (all of which are available from BFGoodrich). The most preferred solvent-borne polyurethane is Sanres EX4991®.

Examples of preferred water-borne polyester polyurethanes include Sancure® 2060 and Sancure® 815 (both of which are commercially available from BFGoodrich).

The most preferred water-borne polyurethanes are aliphatic polyether polyurethanes. Examples of preferred aliphatic polyether polyurethanes include Sancure 2710® and/or Avalure UR 445®, Sancure 878®, NeoRez R-966, NeoRez R-967, and Witcobond W-320.

Preferred cellulosic polymers include, for example, nitrocellulose, cellulose acetate butyrate, and cellulose acetate propionate. The most preferred cellulosic polymer is nitrocellulose. Exemplary nitrocellulose polymers are nitrocellulose RS types (nitrogen content of 11.5% to 12.2%), commercially available from Hercules, such as nitrocellulose RS ½ second, nitrocellulose RS ¼ second, nitrocellulose RS 1/8 second, and nitrocelluose RS 1/16 second, and the like. Wherein a composition comprises a cellulosic polymer, the composition preferably comprises a plasticizer.

The compositions of the present invention further comprise a carrier comprising a liquid diluent. The liquid diluent comprises water, organic solvent, or mixtures thereof. Preferred organic solvents include those which are volatile. Preferred volatile organic solvents, at atmospheric pressure, have a boiling point of from about 50° C. to about 140° C., more preferably from about 56° C. to about 125° C., and most preferably from about 56° C. to about 98° C. Wherein the film-forming polymer utilized is water-borne, the organic solvent is preferably water-miscible.

Preferred organic solvents are selected from alcohols, esters, ketones, aromatic hydrocarbons, aliphatic hydrocarbons, ethers, and mixtures thereof. Alcohols and esters are more preferred. Preferred alcohols are monohydric. The most preferred monohydric alcohols are ethanol, iso-propanol, and n-propanol. The most preferred esters are ethyl acetate and butyl acetate. Other non-limiting examples of suitable organic solvents are benzyl alcohol, amyl acetate, propyl acetate, acetone, heptane, iso-butyl acetate, iso-propyl acetate, toluene, methyl acetate, iso-butanol, n-amyl alcohol, n-butyl alcohol, hexane, and methyl ethyl ketone.

The kits of the present invention may further comprise information which informs a user of the kit, by words, pictures, and/or the like, that use of the kit will provide one or more long wear benefits, including, but not limited to, resistance to chipping, peeling, denting, and/or peeling.

The films herein are formed when a kit of the present invention is applied to mammalian nails. The films of the present invention comprise two or more layers formed from two or more different compositions, most preferably two or three layers formed from two or three different compositions, respectively. The preferred films are those which are comprised of a basecoat and a topcoat, and those which further comprise a midcoat.

The films herein are not peelable from the nails. That is, the films herein, when joined to the nail, cannot be stripped off the nail by simply peeling the film off the nail in a substantially intact form.

The multi-layer films herein form when two or more compositions of the kit, as described herein, are applied to and substantially dry on mammalian nails. The compositions useful herein may be described as basecoat compositions, midcoat compositions, or topcoat compositions, depending on their intended positioning on the nail.

A. Basecoat Compositions

As used herein, a "basecoat composition" is a composition which is suitable for application to a mammalian nail to form a basecoat, which is a layer of nail polish. A basecoat composition is preferably applied contiguously to a mammalian nail with or without, more preferably with, one or more succeeding layers applied to the resulting basecoat. The basecoat composition is preferably applied contiguously to a mammalian nail with one or more, more preferably one (topcoat), and most preferably two (midcoat and topcoat), succeeding layers joined to the resulting basecoat.

Without intending to be limited by theory, it is believed that the basecoats of the present invention are beneficial to long wear because they provide a preferred level of adhesion to the nail. Such adhesion is believed to be due to physical forces, rather than chemical bonding to the nail. As is known in the art, these physical forces include non-covalent interactions such as polar, non-polar, hydrogen bonding, and charged interactions as well as physical interactions such as mechanical interlocking.

Without intending to be limited by theory, such adhesion is largely achieved via the surface energies and/or polarities of the layer of the film which is contiguous to the nail (i.e., the basecoat). Adhesion may be optimized by matching the surface energy and/or polarity of the basecoat to that of the nail, which have been found by the present inventors to be surface energies from about 32 mN/m to about 43 mN/m, more preferably from about 34 mN/m to about 42 mN/m, and polarities from about 0.19 to about 0.29, more preferably from about 0.20 to about 0.24.

Such matching is primarily achieved by selection of the film-forming polymer. Formulation adjustments which may change surface energies and/or polarities of the final film may reduce adhesion between the nail surface and the film-forming polymer in the basecoat. Thus, the film-forming polymer itself is selected, first by general class (polyurethane, polyacryl, e.g.) and second via the chemistry of the monomers present in the film-forming polymer. Preferred polymer classes which achieve the presently defined surface energies and polarities are defined herein. Experimentation within a polymer class, which is well within the purview of the ordinarily skilled artisan, may be utilized to select film-forming polymers having surface energies and polarities which most closely match the defined ranges.

The present basecoat compositions comprise a film-forming polymer, a liquid diluent, and, optionally, one or more other suitable components as described herein. The basecoat compositions preferably comprise from about 0.1% to about 40%, more preferably from about 1% to about 10%, and most preferably from about 2% to about 6% of the film-forming polymer (polymer solids), and preferably from about 10% to about 90%, more preferably from about 40% to about 90%, even more preferably from about 50% to about 90%, and most preferably from about 70% to about 90% of the volatile organic solvent (as described herein above), by weight of the composition. Preferably, the balance of the compositions is substantially water, preferably at least about 4%, more preferably from about 4% to about 85%, still more preferably from about 10% to about 80%, and most preferably from about 25% to about 80%, by weight of the composition, of water.

The film-forming polymers of the basecoat compositions are preferably water-insoluble at ambient temperature and pressure.

Preferred film-forming polymers for use in the basecoat compositions are selected from polyurethanes, polyacryls, polymethacryls, urethane-acryl copolymers, styrene-acryl copolymers, cellulosic polymers, polysiloxanes, and mixtures thereof. The more preferred polymers of basecoat compositions are selected from cellulosic polymers, polyurethanes, polyacryls, polymethacryls, polysiloxanes, and mixtures thereof. Even more preferred polymers of basecoat compositions are selected from polyurethanes, polyacryls, polymethacryls, urethane-acryl copolymers, styrene-acryl copolymers, and mixtures thereof. The most preferred polymers for use in the basecoat compositions are polyurethanes. The most preferred polyurethane for use in basecoat compositions is Sancure 2710® and/or Avalure UR 445®. Preferred types of each of these polymer classes, and examples thereof, are described herein above.

Preferred polyacryls, polymethacryls, and styrene-acryl copolymers for use in the basecoat compositions are those having a glass transition temperature ($T_g$) of from about −30° C. to about +60° C., more preferably from about −20° C to about +20° C. surface energies from about 32 mJ/m$^2$ to about 43 mJ/m$^2$, calculated using the harmonic mean equation (as determined by the Wilhelmy Technique described by A. W. Neumann and R. J. Good, *Surface and Colloid Science*, Vol. 2, R. J. Good and R. R. Stromberg, Eds., Plenum Press (1979)), and/or polarities from about 0.19 to about 0.29.

The most preferred polyacryls and polymethacryls for use in basecoat compositions include Glascol LS20, Glascol C37, Joncryl® 95, and SCX-1965.

The film-forming polymers of the basecoat compositions are preferably solvent-borne or water-borne, most preferably water-borne. Especially preferred are water-borne polymers selected from polyurethanes, polyacryls, polymethacryls, urethane-acryl copolymers, styrene-acryl copolymers, and mixtures thereof.

B. Topcoat Compositions

As used herein, a "topcoat composition" is a composition which is suitable for application to a mammalian nail to form a topcoat, which is a layer of nail polish. The topcoat composition is preferably applied contiguously to, or applied to, one or more preceding layers. The topcoat composition is more preferably applied contiguously to one or two, preferably one (basecoat), and most preferably two (basecoat and midcoat), preceding layers.

Without intending to be limited by theory, it is believed that the topcoats are beneficial to long wear because they deflect environmental stressors by virtue of their hardness, toughness, durability, rigidity, and resistance to chipping. The toughness and/or hardness a film exhibits is an indication of, for example, its capability to absorb energy or to experience deformation with minimized fracture. For nail polish, this is an important element of resistance to deterioration. When applied to mammalian nails, a nail polish film will typically and repeatedly experience bending, impact, and abrasion against other surfaces. A nail polish which is tough, such as the topcoats described herein, will resist failure of the film under these abuses, thus providing longer wear on nails. The properties of toughness and hardness is most useful for topcoats because topcoats come into direct contact with the environment. Accordingly, topcoats exhibit the greatest need for resistance to cohesive failure.

Without intending to be limited by theory, a tough or hard topcoat may be chosen which exhibits strong frequency dependence of its dry film properties, for example G" and G'", over a frequency range of $10^{-04}$ to $10^{+01}$ Hz, thus allowing the topcoat to behave as a (flexible) solid under conditions representative of external wear (e.g., tapping and dragging), but to dissipate viscous energy under conditions such as bending. Properties such as G' and G" are easily measured by one knowledgeable in coatings physical measurements, and are described in detail in many textbooks on the subject. See e.g., *Mechanical Properties of Polymers and Composites*, second ed., Ch. 4 ("Dynamic Mechanical Properties"), Marcel Dekker, Inc. An exemplary composition is set forth in Table A herein below which has been found to have nearly ideal rigidity at $10^{+01}$ Hz after 24 to 48 hours of drying on the nail and to have complementary viscous (i.e., G") properties at frequencies below $10^{-03}$ Hz, as measured on a Perk in Elmer DMA Model with 100 micron thick films measured at 24 and 48 hours of aging, such as described in *Mechanical Properties of Polymers and Composites*, and especially in the references in Chapter 4 ("Dynamic Mechanical Properties").

The present topcoat compositions comprise a film-forming polymer, a liquid diluent, and, optionally, other suitable components as described herein.

The film-forming polymers of the topcoat compositions are preferably either solvent-borne or water-borne and are preferably water-insoluble. Preferred film-forming polymers for topcoat compositions have glass transition temperatures ($T_g$) from about +20° C. to about +100° C., more preferably from about +30° C. to about +80° C.

The preferred film-forming polymers of topcoat compositions of the present invention are selected from polyurethanes, polyacryls, polymethacryls, styrene-acryl copolymers, cellulosic polymers, polyesters, vinyl acetate polymers, polysiloxanes, polystyrene-polyacryl mixtures, siloxane-urethane copolymers, polyurethane-polymethacryl mixtures, silicone-acryl copolymers, and mixtures thereof. The more preferred film-forming polymers of topcoat compositions are selected from cellulosic polymers, polyurethanes, polyacryls, polymethacryls, polysiloxanes, and mixtures thereof. Even more preferred film-forming polymers of topcoat compositions are selected from polyurethanes, polyacryls, polymethacryls, polystyrene-polyacryl mixtures, styrene-acryl copolymers, siloxane-urethane copolymers, cellulosic polymers, polyesters, polyurethane-polymethacryl mixtures, silicone-acryl copolymers, vinyl acetate polymers, and mixtures thereof. The most preferred film-forming polymers of topcoat compositions are polyacryls and polyurethane-cellulosic polymer mixtures. The most preferred polyacryl for use in topcoat compositions is Duraplus 2®. Preferred types of each of these polymer classes, and examples thereof, are referred to herein above.

Preferred solvent-borne film-forming polymers include polyurethane-polymethacryl mixtures, polyurethane-cellulosic polymer mixtures, polyurethanes, polyacryls, polymethacryls, silicone-acryl copolymers, and mixtures thereof, more preferably, polyacryls and polyurethane-cellulosic polymer mixtures, and most preferably polyacryls.

Wherein the film-forming polymer of the topcoat composition is solvent-borne, the topcoat composition preferably comprises from about 1% to about 50%, more preferably from about 10% to about 25% of the film-forming polymer (polymer solids), by weight of the composition. The topcoat composition comprising the solvent-borne polymer preferably further comprises from about 50% to about 99%, more preferably from about 75% to about 90%, by weight of the composition, of a volatile organic solvent (as described herein above).

Wherein the topcoat composition comprises a solvent-borne film-forming polymer, preferred optional components include thickeners, plasticizers, pigments or dyes, resins, and slip aids.

Preferred water-borne film-forming polymers are selected from polyurethanes, polyacryls, polymethacryls, styrene-acryl copolymers, siloxane-urethane copolymers, and mixtures thereof. More preferred water-borne film-forming polymers are selected from polyacryls and styrene-acryl copolymers and the most preferred water-borne film-forming polymers are polyacryls.

Wherein the film-forming polymer of the topcoat composition is water-borne, the topcoat composition preferably comprises from about 1% to about 40%, more preferably from about 5% to about 30%, and most preferably from about 10% to about 25%, by weight of the composition, of the film-forming polymer (polymer solids).

The topcoat composition comprising the water-borne polymer preferably further comprises a coalescent. Preferably, the topcoat composition comprising the water-borne polymer comprises from about 0.1% to about 30%, more preferably from about 1% to about 20%, by weight of the composition, of a coalescent. Preferably, the ratio of water-borne film-forming polymer to coalescent is from about 1:1 to about 4:1.

Wherein the topcoat composition comprises a water-borne film-forming polymer, other preferred optional components include plasticizers, slip aids (especially waxes and surfactants containing siloxanes), thickeners, and pigments or dyes. Topcoat compositions comprising water-borne film-forming polymers may also optionally contain up to about 50%, more preferably from about 5% to about 40%, and most preferably from about 10% to about 30%, by weight of the composition of a volatile organic solvent. Preferred organic solvents are described herein above.

Wherein the topcoat composition comprises a water-borne polymer, the balance of the composition is substantially water.

The film-forming polymers of the present topcoat compositions may be cross-linked polymers. The present inventors have surprisingly discovered that film-forming polymers which are cross-linked provide properties which are particularly advantageous for topcoat compositions and topcoats including, for example, chip-resistance and superior hardness. Cross-linking may occur either in the composition itself or after application and film formation. However, as used herein, polymers which are not actually cross-linked in the composition but may become cross-linked (i.e., "cross-linkable" polymers) due to the presence of a basic moiety (as described herein) are referred to herein as cross-linked polymers.

As used herein, a "cross-linked polymer" is a polymer which is ionically linked either intramolecularly to itself and/or intermolecularly to one or more other polymers wherein the linkage is formed through an ionic bridge between a metallic ion and a basic moiety comprising the polymer. Cross-linked polymers are preferably intermolecularly linked. Suitable metallic ions include those with an oxidation state of +2, +3, +4 or higher and which are soluble in water. Preferred metallic ions are selected from $Zn^{+2}$, $Mg^{+2}$, $Ca^{+2}$, $Fe^{+2}$, $Fe^{+3}$, $Al^{+3}$, $Mn^{+2}$, $Co^{+2}$, and $Ni^{+2}$. More preferred metallic ions are selected from $Zn^{+2}$, $Mg^{+2}$, $Ca^{+2}$, $Fe^{+2}$, $Fe^{+3}$, and $Al^{+3}$. The most preferred metallic ion is $Zn^{+2}$.

The basic moieties herein are negatively charged or otherwise basic. The basic moieties may be either present in, or pendant from, the film-forming polymer backbone. Preferred basic moieties are selected from carboxylates, sulfonates, sulfates, phosphates, phosphonates, hydroxymates, borate esters, imidazoles, α-thioketones, thioacids, and alkyl amines. More preferred basic moieties are selected from carboxylates, sulfonates, sulfates, phosphates, phosphonates, and alkyl amines. Even more preferred basic moieties are selected from carboxylates, sulfonates, sulfates, phosphates, and phosphonates. The most preferred basic moieties are carboxylates.

The most preferred cross-linkable polymers are selected from polyacryls, polymethacryls, styrene-acryl copolymers, styrene-methacryl copolymers, and mixtures thereof. Cross-linked polymers may be commercially obtained (for example, Duraplus 2®). Cross-linked polymers may alternatively be produced by obtaining or synthesizing a polymer comprising a pendant basic moiety and adding to that polymer a metal ion solution such as, for example, Zinc Oxide Solution #1 (containing about 15% metal ion solids, commercially available from S.C. Johnson & Sons, Inc.) or Bacote 20 (commercially available from Magnesium Elektron, Inc., Flemington, N.J.). Wherein a metal ion solution is added, the solution is added in an amount sufficient to react substantially completely with the available basic moieties present on the film-forming polymer. Preferably, the amount of metal ion solids, relative to the polymer solids present in the composition, is from about 0.2% to about 0.7%, more preferably from about 0.3% to about 0.6%, and most preferably from about 0.4% to about 0.5%, by weight of the composition.

Wherein the film-forming polymer is cross-linked, the polymer is most preferably water-borne.

Wherein a topcoat comprises a cross-linked polymer, the topcoat may be removed from the nail by a wash treatment with a chelator solution which selectively pulls metal cross-linking ions out of the film and destroys the film. Suitable chelator solutions are selected based on the type of metal ion utilized. Exemplary solutions include, for example, aqueous solutions of ethylenediamine disuccinic acid.

C. Midcoat Compositions

As used herein, a "midcoat composition" is a composition which is suitable for application to a mammalian nail to form a midcoat, which is a layer of nail polish. The midcoat composition is preferably applied contiguously to a preceding layer, either a basecoat or another midcoat, most preferably a basecoat. One or more succeeding layers is applied to the layer formed by the midcoat composition. Preferably, a topcoat is applied contiguously to the layer formed by the midcoat composition.

The use of midcoats is preferred wherein there are significant differences between the physical and/or mechanical properties of the basecoat and the topcoat. For example, midcoats preferably relax stress between flexible basecoats and tough topcoats and/or provide color.

The present midcoat compositions comprise a film-forming polymer, a liquid diluent, and, optionally, other suitable components as described herein. Preferred optional components for midcoat compositions are selected from plasticizers, pigments, and dyes.

Midcoat compositions preferably comprise from about 10% to about 25%, more preferably from about 10% to about 18% of a film-forming polymer, from about 60% to about 85%, more preferably from about 60% to about 80% of a volatile organic solvent (as described herein above), and preferably 0% to about 13%, more preferably from about 5% to about 13%. and most preferably from about 6% to about 12% of a plasticizer, by weight of the composition.

Film-forming polymers comprising the midcoat compositions are selected from cellulosic polymers, polyurethanes, polyacryls, polymethacryls, polysiloxanes, and mixtures thereof. More preferred film-forming polymers are polyacryls and cellulosic polymers, with cellulosic polymers being the most preferred. Preferred types of each of these polymer classes, and examples thereof, are described herein above.

Preferred polyacryls for the midcoat compositions are those which are hydrophobic and/or exhibit a glass-transition temperature ($T_g$) of from about $-10°$ C. to about $+30°$ C. Wherein the polyacryl has a $T_g$ higher than about $+30°$ C., the midcoat composition preferably comprises a plasticizer.

Exemplary compositions suitable for use as midcoat compositions are commercially available such as, for example, those marketed under the Max Factor® or Cover Girl® trade names.

Optional Components

The compositions of the kits of the present invention may, independently, comprise additional optional components to enhance their performance as a nail polish. For example, antifoams, buffers, chelating agents, coalescents, dispersing agents, dyes, epoxies, fillers, pigments, preservatives, resins, therapeutic and prophylactic agents, thickeners, wax additives, wetting agents, and the like can be included in the compositions herein. Such optional components may be dispersed, solubilized, or otherwise mixed in the carrier and/or the liquid diluent of the compositions. These components may be added to the compositions herein provided they do not substantially hinder the long wear of the kits. Non-limiting examples of optional components are given below.

Coalescents

Coalescents may optionally be added to the compositions to enhance film-formation, most preferably wherein the film-forming polymer is water-borne. Such coalescing aids are known in the art and are typically glycol ethers or glycol ether esters such as $C_{1-10}$, straight or branched chain alkyl glycol alkyl ethers, $C_{1-10}$ straight or branched chain alkyl ether acetates, di-$C_{1-10}$ alkyl ether acetates, and $C_{1-10}$ ioalkyl glycol phenyl ethers. Preferred coalescing aids include, for example, ethylene glycol ethers (e.g., Dowanol EB®, commercially available from Dow Chemical Co.), diethylene glycol ethers, triethylene glycol ethers, propylene glycol ethers (e.g., Dowanol PnP®, Dow Chemical Co.), dipropylene glycol ethers (e.g., Dowanol DPnP®, Dow Chemical Co.), tripropylene glycol ethers, terpenes, camphor, methyl cellusolve, butyl cellusolve, hexyl cellusolve, methyl carbitol, butyl carbitol, and dibutyl phthalate.

Preferably, a composition comprises from 0% to about 10%, more preferably from about 0.1% to about 10%, by weight of the composition, of a coalescent.

Pigments or Dyes

Pigments and other suitable coloring agents, such as dyes, may be incorporated into the compositions. Suitable pigments are inorganic or organic pigments known as, for example, the FD&C and D&C colors, lakes, and iron oxides. Such pigments are disclosed in the C.T.F.A. *Cosmetic Ingredient Handbook*, First Edition, 1988. Organic pigments include, for example, D and C Red, Nos. 10, 11, 12, and 13, D and C Red No. 7, D and C Red Nos. 5 and 6, D and C Red Nos. 30 and 34, lacquers such as D and C Yellow No 5 and D and C Red No. 2, and guanine. Inorganic pigments include, for example, titanium dioxide, bismuth oxychloride, brown iron oxide, and the red iron oxides.

Preferably, the present compositions comprise from 0% to about 5%, more preferably from 0% to about 2%, and most preferably from 0% to about 1%, by weight of the composition, of a pigment or dye.

Plasticizers

Without intending to be limited by theory, plasticizers cause a composition to become more easily deformed. One or more plasticizers may optionally be added to the present compositions. Suitable plasticizers include those disclosed in WO 97/00664, Chen et al, assigned to Eastman Chemical Co. Suitable plasticizers include phthalates, nonionic surfactant polymers, camphor, castor oil, sucrose acetate isobutyrate, alkyl toluenesulfonamides, e.g., ethyl toluenesulfonamide (e.g., Uniplex PX-45, commercially available from Unitex Chemical Corp., Greenboro, N.C.), and polyester acid derivatives (e.g., Uniplex 670P, commercially available from Unitex Chemical Corp.), particularly polyester di- and tri-acids. Preferred plasticizers include diethyl phthalate, dibutyl phthalate, dioctyl phthalate, diethyl tartrate, dibutyl tartrate, diethyl phosphate, dibutyl phosphate, polyester sebacates, such as Paraplex G-25® (commercially available from C.P. Hall, Bedford Park. Ill.) polyester adipates, such as Paraplex G-50® (C.P. Hall) and tetraethylene glycol di-2-ethylhexoate, available as Tegmer® (C.P. Hall). The most preferred plasticizers include dibutyl phthalate, Paraplex G-250®, Paraplex G-50®, camphor, Uniplex PX-45, and Tegmer®.

A composition preferably comprises from 0% to about 15%, more preferably from 0% to about 10%, and most preferably from 0% to about 5%, by weight of the composition, of a plasticizer.

Preservatives

One or more preservatives may optionally be added to the present compositions to prevent, inhibit, or retard microbial growth in the composition. Preferred preservatives include methyl paraben, ethyl paraben, propyl paraben, benzyl alcohol, benzoic acid, benzoates (preferably sodium benzoate), sorbates (preferably potassium sorbate), sodium dehydroacetate, 1-(3-chloroallyl)-3,5,7-triaza-1-azoniaadamantane chloride (which may be obtained commercially as Quaternium-15® from Dow Chemical Co., Midland, Mich.), a mixture of 95% 1,3-dimethylol-5,5-dimethyl hydantoin and 5% 3-iodo-2-propynyl butyl carbamate (which mixture is commercially available as Glydant Plus® from Lonza, Inc., Fair Lawn, N.J.), 1,3-dimethylol-5,5-dimethyl hydantoin (commercially available as Glydant® from Lonza, Inc.), diazolidinyl urea (commercially available as Germall II® from Sutton Laboratories, Chatham, N.J.), imidazolidinyl urea (commercially available as Germall 115® from Sutton Laboratories), phenoxyethanol, and Kathon® (commercially available from Rohm and Haas Co., Philadelphia, Pa.). The most preferred preservatives include methyl paraben, ethyl paraben, propyl paraben, benzyl alcohol, benzoic acid, benzoates (preferably sodium benzoate), sorbates (preferably potassium sorbate), and sodium dehydroacetate.

A composition preferably comprises from 0% to about 10%, more preferably from 0% to about 5%, and most preferably from 0% to about 1%, by weight of the composition, of a preservative.

Resins

Resins including, for example, epoxies and polyacrylics, may optionally be added. Examples of suitable resins include Polytex E75® (commercially available from Estron Chemical, Inc., Calvert City, Ky.) and Acryloid B66® (commercially available from Rohm and Haas, Philadelphia, Pa.).

A composition preferably comprises from 0% to about 15%, more preferably from about 0.5% to about 10%, by weight of the composition, of a resin.

Slip Aids

Slip aids may optionally be added to improve surface friction, water resistance, abrasion resistance, and mechanical properties. Slip aids which may be used include wax additives including, for example, animal, fossil, vegetable, mineral or synthetic waxes. Preferred wax additives include beeswax, carob, candelilla, ozocerite, polyethylene waxes, paraffin waxes, polypropylene waxes, polytetrafluoroethylene (commercially available as Teflon® from DuPont, Wilmington, Del.), nylons, and polyamides. Specifically, preferred wax additives include, but are not limited to, Jonwax® 26 (commercially available from S.C. Johnson Polymer, Sturtevant, Wis.) Jonwax® 120 (S.C. Johnson Polymer), Chemcor 325N35, Chemcor 43N40, Glaswax® E-1 (commercially available from Allied Colloids, Suffolk, Va.), Glaswax® E-1235 (Allied Colloids), Drewax® E-3030 (commercially available from Ashland Chemical, Boontown, N.J.), Drewax® E-7030 (Ashland Chemical), Lanco® PP1362D (commercially available from Lubrizol, Wichliffe, Ohio.), Lanco® Al 601 (Lubrizol), and Lanco® TF1780 (Lubrizol).

Other slip aids include materials containing silicone such as copolymers of polyether and polysiloxane. Examples of such slip aids include, for example, Glide 450 and Abil B-8830 (both of which are commercially available from Goldschmidt Chemical, Hopewell, Va.).

The present compositions preferably comprise from 0% to about 10%, more preferably from about 0.1% to about 10%, even more preferably from about 0.5% to about 8%, and most preferably from about 0.5% to about 3% of a slip aid.

Stabilizers

One or more stabilizers may be added to the compositions herein, e.g., to prevent pigment from settling or to achieve desired application properties. Preferably, stabilizers are added to compositions comprising a solvent-borne film-forming polymer. Preferred stabilizers include clays, e.g., organically modified bentonites and hectorites such as stearalkonium bentonite and stearalkonium hectorite (commercially available from Rheox, Inc., Hightstown, N.J.).

Wherein a stabilizer is added, the composition preferably comprises from about 0.25% to about 3%, still more preferably from about 0.25% to about 2.5%, and most preferably from about 1% to about 2% of the stabilizer, by weight of the composition.

Therapeutic and Prophylactic Agents

Therapeutic and/or prophylactic agents such as, for example, vitamins, proteins, anti-fungal and anti-microbial agents, and sunscreens (including UV-A, UV-B, and broad spectrum solar filters) may optionally be added to the present compositions for the further care and protection of the nails.

Thickeners

Thickeners may optionally be added to the compositions and films herein to achieve desired rheology and application properties. Preferably, thickeners are utilized wherein the composition comprises a water-borne film-forming polymer or at least 4% water. Preferred thickeners include hydroxyethyl cellulose, hydroxypropyl cellulose, methyl cellulose, and other conventional cellulosic polymers, associative thickeners (e.g., hydrophobically modified cellulosic polymers, nonionic urethanes, and alkali swellable urethanes) including Aculyn® 44 (commercially available from Rohm & Haas, Philadelphia, Pa.), clays (e.g., laponite and hydrophilic montmorillonite (commercially available as Bentonel from Rheox, Hightstown, N.J.), and natural rubbers and gums (e.g., guar gum, quaternized guar gum sold under the name Jaguar® C-13-S by Rhone-Poulenc, Shelton, Con.), hydroxypropyl guar gum, gum arabic, carob gum, carrageenan, and xanthan gum).

The present compositions preferably comprise from 0% to about 10%, more preferably from about 0.1% to about 10%, and even more preferably from about 0.1% to about 5% of a thickener, by weight of the composition.

Preferred Kits of the Present Invention

The kits herein are comprised of two or more separate and different compositions, most preferably two or three separate and different compositions. Preferably, the kits are comprised of at least one of a basecoat composition, a midcoat composition, and/or a topcoat composition. More preferably, the kits are comprised of a basecoat composition, a topcoat composition, and, optionally, a midcoat composition.

A preferred kit ("kit 1") having two separate and different compositions comprises a basecoat composition and a topcoat composition. The basecoat composition of kit 1 comprises a film-forming polymer, preferably a water-insoluble polymer, which is selected from polyurethanes, polyacryls, polymethacryls, urethane-acryl copolymers, styrene-acryl copolymers, and mixtures thereof. The topcoat composition of kit 1 comprises a film-forming polymer, preferably a water-insoluble polymer, which is selected from polyurethanes, polyacryls, polymethacryls, polystyrene-polyacryl mixtures, styrene-acryl copolymers, siloxane-urethane copolymers, cellulosic polymers, polyesters, polyurethane-polymethacryl mixtures, silicone-acryl copolymers, vinyl acetate polymers, and mixtures thereof.

Another preferred kit ("Kit 2") having three separate and different compositions comprises the basecoat composition and topcoat composition as described for Kit 1, and further comprises a midcoat composition. The midcoat composition of Kit 2 comprises a film-forming polymer, preferably a water-insoluble polymer, which is selected from cellulosic polymers, polyurethanes, polyacryls, polymethacryls, polysiloxanes, and mixtures thereof.

Another preferred kit ("Kit 3") having two separate and different compositions comprises a basecoat composition and a topcoat composition. The basecoat composition of Kit 3 comprises a film-forming polymer, preferably a water-insoluble polymer, which is selected from polyurethanes, polyacryls, polymethacryls, urethane-acryl copolymers, styrene-acryl copolymers, and mixtures thereof. The topcoat composition of Kit 3 comprises a film-forming polymer, preferably a water-insoluble polymer, which is selected from cellulosic polymers, polyurethanes, polyacryls, polymethacryls, polysiloxanes, and mixtures thereof.

Another preferred kit ("Kit 4") having two separate and different compositions comprises a basecoat composition and a topcoat composition. The basecoat composition of Kit 4 comprises a film-forming polymer, preferably a water-insoluble polymer, which is selected from cellulosic polymers, polyurethanes, polyacryls, polymethacryls, polysiloxanes, and mixtures thereof. The topcoat composition of Kit 4 comprises a film-forming polymer, preferably a water-insoluble polymer, which is selected from polyurethanes, polyacryls, polymethacryls, polystyrene-polyacryl mixtures, styrene-acryl copolymers, siloxane-urethane copolymers, cellulosic polymers, polyesters, polyurethane-polymethacryl mixtures, silicone-acryl copolymers, vinyl acetate polymers, and mixtures thereof.

Method of Making and Using

The compositions of the present invention are made using conventional formulation and mixing techniques. A layer of nail polish may be prepared by standard application of a composition to mammalian nails using a standard brush-applicator as is commonly utilized in the art and removing sufficient liquid diluent (through evaporation of volatiles, most preferably at ambient pressures and temperatures) to form the substantially dry layer. The multi-layer films of the present invention are prepared in a similar manner by standard application of one or more additional compositions contiguously to the preceding layer. Such application is well-known in art.

The present invention includes a method of coating mammalian nails with a nail polish film, wherein the film comprises two or more layers. The method comprises the steps of:

(i) applying a basecoat composition contiguously to the nail, wherein the basecoat composition comprises a film-forming polymer and a liquid diluent;

(ii) removing sufficient liquid diluent from the basecoat composition to form a substantially dry basecoat;

(iii) optionally applying a midcoat composition to the basecoat, wherein the midcoat composition comprises a film-forming polymer and a liquid diluent;

(iv) removing sufficient liquid diluent from the midcoat composition to form a substantially dry layer;

(v) applying a topcoat composition to the basecoat (or the layer formed by the midcoat composition, if used), wherein the topcoat composition comprises a film-forming polymer and a liquid diluent; and (vi) removing sufficient liquid diluent from the topcoat composition to form a substantially dry topcoat;

wherein the film exhibits a Total Wear Index and/or a Tip Wear Index of less than about 0.90, more preferably less than about 0.80, and most preferably less than about 0.70, and/or a Jagged Index of less than about 0.90, more preferably less than about 0.85, and most preferably less than about 0.80.

Properties of Films of the Present Invention

Known nail polishes tend to exhibit deterioration on the nail after a short period of use. The present inventors have surprisingly discovered kits which provide films exhibiting long wear. Such long wear is experienced over the entire surface of the nail and is quantitatively expressed herein by the Total Wear Index for a particular nail polish. Furthermore, the present inventors have discovered kits and films which, when applied to the nail, exhibit long wear particularly at the tip of the nail. Such long wear is quantitatively expressed herein by the Tip Wear Index for a particular nail polish. Still further, wherein deterioration is exhibited by the present kits and films, deterioration progresses in an even, smooth fashion relative to the uneven, jagged deterioration which tends to be exhibited by nail polishes known in the art. Such wear is quantitatively expressed herein by the Jagged Index for a particular nail polish.

As used herein, the lower the Total Wear Index and/or Tip Wear Index for a particular nail polish, the less deterioration is exhibited by that nail polish, relative to a control nail polish. The lower the Jagged Index, the more even and smooth is the deterioration exhibited by that particular nail polish, as compared to a control nail polish. The kits of the present invention provide films exhibiting a Total Wear Index and/or Tip Wear Index of less than about 0.90, more preferably less than about 0.80, even more preferably less than about 0.70, and most preferably less than about 0.65, and/or a Jagged Index of less than about 0.90, more preferably less than about 0.85, and most preferably less than about 0.80.

Total Wear Indices, Tip Wear Indices, and Jagged Indices are determined using the following test method.

Human female subjects are chosen who are accustomed to applying nail polish to, and wearing nail polish on, their own nails and who do not use synthetic nails such as, for example, acrylic nails. Individuals are initially categorized according to the percentage of total deterioration (as defined herein below) they typically experience with nail polish by following this complete method using the control product on all ten fingers. The formula of the control product is given in Table A below. Individuals who exhibit greater than 12% total deterioration after 5 days of normal use without touch-up, as measured by this method, are designated heavy stressors; individuals who exhibit between 6% and 12% total deterioration are designated moderate stressors; and individuals who exhibit less than 6% total deterioration are designated light stressors. Following this method, a subject group of approximately twenty subjects (not less than sixteen) is selected which contains about one-third heavy and one-third moderate stressors, and no more than one-third light stressors.

TABLE A

Control Product

| Component | Supplier Slurry Code* | Source | Percentage |
|---|---|---|---|
| Solid Nitrocellulose RS ¼ second (available as a slurry) | 50-C3-690 | Akzo Nobel, Somerset, NJ | 7.05% |
| Solid Nitrocellulose RS ½ second (available as a slurry) | 5528 | Scholle Corp., College Park, GA | 7.00% |
| Clay** (available as a slurry) | Bentone slurry | Kirker Enterprises Inc., Paterson, NJ | 1.04% |
| Red #7 Solid (available as a slurry) | Red #7 Slurry 6R381 | Penn Color, Doylestown, PA | 0.60% |
| Butyl Acetate | | J. T. Baker, Phillipsburg, NJ | 27.77% |
| Ethyl Acetate | | J. T. Baker, Phillipsburg, NJ | 24.00% |
| iso-Propanol | | J. T. Baker, Phillipsburg, NJ | 6.55% |
| Uniplex 600 | | Unitex, Greensboro, NC | 11.12% |
| Toluene | | E.M. Science, Gibbstown, NJ | 6.44% |
| Camphor | | Universal Preservachem, Edison, NJ | 1.43% |
| Dibutyl Phthalate | | Eastman Kodak, Kingsport, TN | 7.00% |
| Total | | | 100% |

*The slurries contain, in addition to the component indicated, other components which are listed in the above formula (such as, for example, butyl acetate and iso-propanol). The percentage given for each component is the percentage of that component only (for example, Solid Nitrocellulose RS ¼ second is present in the control formula at a solids level of 7.05%, exclusive of other components). The levels of the other components in each slurry are combined and reflected in the formula given above. For example, the levels of butyl acetate in Nitrocellulose RS ¼ second slurry, Nitrocellulose RS ½ second slurry, clay, and Red #7 Solid are combined and reflected in the percentage given for the butyl acetate component.
**Clay is 50/50 (weight percent ratio) stearalkonium hectorite/stearalkonium bentonite solids.

The control product is prepared as follows. Weigh all components together into a sealable jar to hold a 100 gram batch with minimal head-space. Add six stainless steel balls, each of which are 3/16 inches in diameter. Mix on a conventional paint shaker for thirty minutes. Transfer to conventional nail polish bottles.

Application of nail polish takes place in a room maintained at a controlled temperature between 70° F. and 75° F., in the morning on a Friday. Subjects wash their hands, dry them, and allow at least ten minutes before application of nail polishes. No nail pre-treatments, mechanical or otherwise, are done or allowed on the nails prior to application.

An alternate finger method of application is employed as follows. The fingers are numbered sequentially, one through ten, from the left pinky finger to the right pinky finger. The odd numbered fingers are denoted "A" fingers; even numbered fingers denoted "B" fingers. Subjects are randomly assigned to wear the control product on either the "A" fingers or the "B" fingers, dividing the subject group in half such that two subject groups are formed. The two subject groups are balanced so that the number of right-handed and left-handed individuals is the same in the group applying the control product to the "A" fingers as the group applying the control product to the "B" fingers. Each subject is given a weighed, numbered bottle of the control product and a timer, and is instructed to apply a coat of nail polish to the designated fingers (either the "A" or "B" set), allow the coat to dry (forming a layer) for five minutes, and then apply a second coat of the control product contiguous to the first layer, applying the polish as the subject normally would. The average weight of the control product applied for five fingers by this process should be about 225 milligrams but will vary depending on the size of each subject's nails.

Each subject is then given the nail polish to be tested (test nail polish) and is instructed to apply it in the above manner to the five fingers which were not coated with the control product (the remaining fingers). Test nail polishes of the present invention comprise two or more different nail polish compositions. Wherein two or more nail polish compositions are to be applied, a test coordinator instructs the subjects as to the order of application. For convenience of subsequent capturing of images and analysis, a brightly colored red nail polish may be used, but this method is not limited by color of the nail polish. Test nail polishes that are not colored or are insufficiently opaque to adequately distinguish them from the nail as required for subsequent image grabbing are tested by incorporating one or more suitable dyes or pigments in the test nail polish at a level sufficient to see the color of the film and differentiate it from the color of the nail. After applying the test nail polish to the designated fingers in the order and manner instructed, application is complete and individuals are instructed not to damage the nail polishes as they continue to set over the next two to three hours. The subjects attend to their usual activities until they return for image taking.

On the Wednesday following application of the nail polish, subjects return to have images of their nails taken. Beginning with finger number one and proceeding through finger number ten, each subject places the palm of her hand on a flat surface on which a transom, or finger rest (described below), is positioned underneath a camera to capture an image of each fingernail, without axial rotation and without pressure except due to the weight of the finger. This positioning allows optimum lighting to all areas of the nail, and a reproducible fingernail area to be presented to the camera for imaging.

Images are taken with a Zeiss SV-11 stereomicroscope and a Sony 3-C-CD camera (or equivalents thereof). A 1.0 zoom ring is used, with a ¼× lens, the working distance above the finger set by focus (approximately 37 cm). Magnification is approximately 15×. A Fostec 8375 (EJA) light ring (or equivalent thereof) is placed 3.5 cm above the finger rest base, and is set at 70% of maximum power. At the bottom, a dark green finger positioning transom on the tabletop is used as a rest for the finger being imaged. The wedge-shaped transom slopes up from front to back, measuring 5 mm in height off the tabletop in front and 12 mm in height off the tabletop in back over a span of 8 cm. Two polarizing filters are used, set in crosspole position to eliminate shine from the nail surface. Optimas 4.1 software (obtainable from Optimas Corp., Bothell, Wash.) is used for image grabbing (or a suitable equivalent thereof). All lighting, camera and software settings are maintained constant through a study. Software contrast and brightness settings are optimized at the start of the study to maximize contrast between the nail and nail polish, and to determine if any colorants or opacifiers need to be added as described herein above.

Percent deterioration analysis is based on area measurement of nail polish remaining on the nail, in a manner similar to the method of analysis of second-phase constituents of metals as described in ASTM E1245–95, "Standard Practice for Determining the Inclusion or Second-Phase Constituent Content of Metals by Automatic Image Analysis". There are three steps involved in analysis of nails for percent deterioration. First, the total area of the nail is determined. Second, the north-south center line of the nail is determined. Third, the remaining polish area is determined in both halves of the nail; and also is categorized as to whether it adjoins a nail edge, and the percentage of tip deterioration, cuticle deterioration, and internal deterioration of an individual nail is determined.

To start, a suitable image is retrieved for viewing on the computer screen. That is, the image must be sufficiently large and of sufficient quality to allow an operator to easily determine by eye the location of all nail edges and all edges of the nail polish. The working image presented to the operator should be magnified approximately 10–15 times actual size, and the entire image must be evenly lit, with no shadows around the nail-cuticle boundary. The image should be bright enough so that the edges of polish and the nail are easily visible to the eye, with high resolution comparable to that of 35 mm film printed on photograph quality paper, or alternatively a 640×480 pixel on-screen digital color image.

As an operator identifies by sight the field of the nail, a computer program such as Optimas 4.1 is used to measure area and perform calculations by the following method. Many such computer programs are available or can be tailored to perform the functions described herein, as is known by one skilled in the field of image analysis and as described in § 12.4.1 of ASTM E1245–95.

The total nail area is determined by tracing the outline of the nail with a cursor on the computer screen controlled by a mouse. The nail is traced exclusive of cuticle or other finger skin. After tracing the entire nail, the total nail area is determined by the Optimas software in dimensionless units. This measurement is referred to herein as $A_m$ ("area of the measurement field" in ASTM E1245–95).

Second, the image is divided in half in north-south directions (i.e., the north half-field comprises the whole tip of the nail and the south half-field comprises the whole edge of the nail adjoining the cuticle), by area. The total area of each half-field is $A_t$. Third, area of nail polish deterioration in each half is determined using a suitable image analysis detection software program that detects only the nail polish covered (colored or opacified) area ($A_c$) (such as, for example, Optimas 4.1). Percent wear for each half-field ($P_{1/2}$) is expressed as:

$$P_{1/2}=[(A_t-A_c)\div A_m]*100\%$$

The percentages derived from each half are added together to give a percent total deterioration for a given finger.

The ability of the image analysis software to accurately detect the nail polish area must be manually verified, such as described in § 12.2.1 of ASTM E1245-95. This measurement is obtained for each nail, individually.

The Total Wear Index for a test nail polish is determined as follows. For each subject, the average percent total deterioration for the test nail polish ($TW_{a1}$) (calculated by adding the percent total deterioration for each of the five fingers having test nail polish applied to them and dividing this by five) is determined. The average percent total deterioration for the test nail polish for the subject group ($TW_{ta1}$) is then determined. Similarly, for each subject, the average percent total deterioration for the control product ($TW_{a2}$) (calculated by adding the percent deterioration for each of the five fingers having the control product applied to them and dividing by five) is determined. The average percent total deterioration for the control product for the subject group ($TW_{ta2}$) is then determined. The Total Wear Index for the test nail polish ($TWI_{test}$) is then calculated as follows:

$$TWI_{test}=TW_{ta1}\div TW_{ta2}$$

Accordingly, the lower the Total Wear Index, the better the wear properties are for that particular nail polish relative to the control product.

In each half of the field, the deterioration area is then calculated as 100% minus the remaining polish area, also expressed as a percentage. The deterioration areas are categorized as to whether they adjoin an outside edge of the nail, or not. Deterioration which does not adjoin an outside edge of the whole nail, being completely enclosed by nail polish, is separately calculated and expressed as internal deterioration. Deterioration in the north half of the nail that adjoins a nail edge is expressed as percent tip deterioration, and is expressed as a percentage based on the area of the whole nail.

The Tip Wear Index for a test nail polish is determined as follows. For each subject, the average percent tip deterioration for the test nail polish ($PW_{a1}$) is determined (calculated by adding the percent tip deterioration for each of the five fingers having test nail polish applied to them and dividing this by five). The average percent tip deterioration for the test nail polish for the subject group ($PW_{ta1}$) is then determined. Similarly, for each subject, the average percent tip deterioration for the control product ($PW_{a2}$) is determined (calculated by adding the percent deterioration for each of the five fingers having the control product applied to them and dividing by five). The average percent tip deterioration for the the control product for the subject group ($PW_{ta2}$) is then determined. The Tip Wear Index for the test nail polish ($PWI_{test}$) is then calculated as follows:

$$PWI_{test}=PW_{ta1}\div PW_{ta2}$$

Accordingly, the lower the Tip Wear Index, the better the wear properties are for that particular nail polish, at the tip of the nail, relative to the tip deterioration exhibited by the control product.

The Jagged Index for a test nail polish is determined as follows. Optimas 5.2 software (obtainable from Optimas Corp., Bothell, Wash.), or an equivalent thereof, is used to automatically determine the perimeter of the nail polish and divide the area into north and south halves by area, as done earlier in the percent deterioration analyses. Optimas 5.2 is capable of smoothing the perimeter to different degrees by being assigning "segment joining values". Assigning a low value results in little smoothing; assigning a high value results in more smoothing. For nail polish edges that have deteriorated in a smooth (even) pattern, the perimeter length will measure nearly the same value regardless of degree of smoothing by Optimas 5.2 For nail polish edges that have deteriorated in a jagged (uneven) pattern, the less smoothed perimeter will be longer than the more smoothed perimeter, which is the basis for the Jagged Index.

Using the captured nail images as described above and Optimas 5.2 (or equivalent thereof), the perimeter of the nail polish in the north half of the nail is measured with segment joining values of both 500 and 2,000, separately. The perimeter derived from using the segment joining value of 500 is designated the "less smoothed perimeter length" ($Pl_u$). The perimeter derived from using the segment joining value 2,000 is designated the "more smoothed perimeter length" ($Pl_s$). An index for that nail ($I_n$) is calculated according to the following equation:

$$I_n = [(Pl_u/Pl_s) - 1] \times 100\%$$

An $I_n$ for each nail is determined in the above manner for all the individual nails for each of the subjects. The average $I_n$ for the nails having test nail polish applied ($I_t$), and the average $I_n$ for those nails having the control product applied ($I_M$) is determined. The Jagged Index for the test nail polish is then calculated according to the following formula:

$$\text{Jagged Index} = I_t \div I_M$$

Accordingly, the lower the Jagged Index, the more even and smooth is the tip deterioration exhibited by that particular nail polish as compared to the control product.

EXAMPLES

The following examples further describe and demonstrate embodiments within the scope of the present invention. The examples are given solely for the purpose of illustration and are not to be construed as limitations of the present invention, as many variations thereof are possible without departing from the spirit and scope of the invention.

In the examples below, all polymer component percentages are expressed in weight percent of solid polymer (based on the total composition).

Examples 1A–1H

The compositions of Examples 1A–1H are suitable for use as basecoat compositions:

Examples 2A–2E

The compositions of Examples 2–2E are suitable for use as topcoat compositions:

|  | 2A | 2B | 2C | 2D | 2E |
|---|---|---|---|---|---|
| Duraplus 2 ® | 21% | — | — | 21% | — |
| Nitrocellulose RS ¼ second | — | 15% | — | — | 6.75% |
| Sanres ® EX499 | — | 3.6% | — | — | — |
| Sanres ® 12711 | — | 1.5% | 15.5% | — | — |
| Sanres ® 6012 | — | — | — | — | 8.25% |
| Surcol ® 441 | — | — | 4.5% | — | — |
| Dowanol DPnP ® | 10% | — | — | 10% | — |
| Dibutyl Phthalate | 3.9% | — | — | 1.6% | — |
| Glide 450 ® | 0.3% | — | — | 0.3% | — |
| Aculyn 44 ® | 0.5% | — | — | — | — |
| Polytex E-75 ® | — | 1% | — | — | — |
| Drewax E-3030 ® | — | — | — | 1.2% | — |
| Paraplex G-50 ® | — | 7.6% | — | — | — |
| Butyl Acetate | — | 30.9% | 28% | — | 38% |
| Ethyl Acetate | — | 27.4% | 10% | — | — |
| iso-Propanol | — | 11% | 30% | — | 35% |
| Toluene | — | — | — | — | 10% |
| Acetone | — | — | 10% | — | — |
| Pigment | — | 1% | 1% | — | 1% |
| Clay | — | 1% | 1% | — | 1% |
| Water | 64.3% | — | — | 65.9% | — |

Example 3

A kit comprising two separate nail polish compositions is prepared. The compositions are a basecoat composition of Example 1 and a topcoat composition of Example 2. The basecoat composition is applied contiguously to mammalian nails using a standard brush-applicator. A basecoat is allowed to form over a period of five minutes. The topcoat composition is applied contiguously to the basecoat using a standard brush-applicator. The topcoat composition is allowed to form a topcoat over a five minute time period, resulting in a film having two layers.

Example 4

A kit comprising two separate nail polish compositions is prepared. The compositions are a basecoat composition of Example I and a topcoat composition which is a conventional nail polish such as Max Factor® International (comprising butyl acetate, ethyl acetate, nitrocellulose, toluenesulphonamide formaldehyde resin, dibutyl phthalate, toluene, iso-propanol, camphor, benzophenone, stearalkonium hectorite, and polyester resin). The basecoat composition is applied contiguously to mammalian nails using a standard brush-applicator. A basecoat is allowed to form

|  | 1A | 1B | 1C | 1D | 1E | 1F | 1G | 1H |
|---|---|---|---|---|---|---|---|---|
| Sancure 2710 ® | 5.5% | 4% | 5.8% | 5.81% | 5.4% | — | 5.74% | 5.74% |
| Glascol LS20 ® | — | — | — | — | 5.7% | — | — | — |
| NeoRez R967 ® | — | — | — | — | — | 5.87% | — | — |
| Ethanol | 7.9% | — | — | — | — | — | — | — |
| iso-Propanol | — | — | — | 32.13% | 44.9% | 65.8% | 65.83% | 46.99% |
| Ethyl Acetate | 78.1% | — | — | — | — | — | — | — |
| n-Propanol | — | 71.6% | 70.0% | — | — | — | — | — |
| Methyl Paraben | — | — | 0.1% | 0.21% | — | 0.1% | 0.2% | 0.2% |
| Propyl Paraben | — | — | 0.1% | — | 0.2% | — | — | — |
| Water | 8.5% | 24.4% | 24.0% | 61.85% | 43.8% | 28.23% | 28.23% | 47.07% | over a period of five minutes. The topcoat composition is applied contiguously to the basecoat using a standard brush-applicator. The topcoat composition is allowed to form a topcoat over a five minute time period, resulting in a film having two layers.

Example 5

A kit comprising two separate nail polish compositions is prepared. The compositions are a basecoat composition which is a conventional nail polish, such as Max Factor® International (comprising butyl acetate, ethyl acetate, nitrocellulose, toluenesulphonamide formaldehyde resin, dibutyl phthalate, toluene, iso-propanol, camphor, benzophenone, stearalkonium hectorite, and polyester resin) and a topcoat composition of Example 2. The basecoat composition is applied contiguously to mammalian nails using a standard brush-applicator. A basecoat is allowed to form over a period of five minutes. The topcoat composition is applied contiguously to the basecoat using a standard brush-applicator. The topcoat composition is allowed to form a topcoat over a five minute time period, resulting in a film having two layers.

Example 6

A kit comprising three separate nail polish compositions is prepared. The compositions are a basecoat composition of Example 1, a midcoat composition which is a conventional nail polish, such as Max Factor® International (comprising butyl acetate, ethyl acetate, nitrocellulose, toluenesulphonamide formaldehyde resin, dibutyl phthalate, toluene, iso-propanol, camphor, benzophenone, stearalkonium hectorite, and polyester resin) and a topcoat composition of Example 2. The basecoat composition is applied contiguously to mammalian nails using a standard brush-applicator. A basecoat is allowed to form over a period of five minutes. The midcoat composition is applied contiguously to the basecoat using a standard brush-applicator. The midcoat composition is allowed to form a layer over a period of five minutes, resulting in a film having two layers. The topcoat composition is applied contiguously to the layer formed from the midcoat composition using a standard brush-applicator. The topcoat composition is allowed to form a topcoat over a period of five minutes, providing a film having three layers.

Example 7

A kit comprising two separate nail polish compositions is prepared. The compositions are a basecoat composition of Example 1 the topcoat composition as set forth in Table A. The basecoat composition is applied contiguously to mammalian nails using a standard brush-applicator. A basecoat is allowed to form over a period of five minutes. The topcoat composition is applied contiguously to the basecoat using a standard brush-applicator. The topcoat composition is allowed to form a topcoat over a five minute time period, resulting in a film having two layers.

What is claimed is:

1. A nail polish film comprising two or more layers wherein each layer comprises a film-forming polymer, wherein the film exhibits a Tip Wear Index of less than about 0.90.

2. A film according to claim 1 comprising a basecoat and a topcoat wherein:
 (a) the basecoat comprises a film-forming water-insoluble polymer selected from the group consisting of polyurethanes, polyacryls, polymethacryls, urethane-acryl copolymers, styrene-acryl copolymers, and mixtures thereof; and
 (b) the topcoat comprises a film-forming water-insoluble polymer selected from the group consisting of polyurethanes, polyacryls, polymethacryls, polystyrene-polyacryl mixtures, styrene-acryl copolymers, siloxane-urethane copolymers, cellulosic polymers, polyesters, polyurethane-polymethacryl mixtures, silicone-acryl copolymers, vinyl acetate polymers, and mixtures thereof.

3. A film according to claim 1 comprising a basecoat and a topcoat wherein:
 (a) the basecoat comprises a film-forming water-insoluble polymer selected from the group consisting of polyurethanes, polyacryls, polymethacryls, urethane-acryl copolymers, styrene-acryl copolymers, and mixtures thereof; and
 (b) the topcoat comprises a film-forming water-insoluble polymer selected from the group consisting of cellulosic polymers, polyurethanes, polyacryls, polymethacryls, polysiloxanes, and mixtures thereof.

4. A film according to claim 1 comprising a basecoat and a topcoat wherein:
 (a) the basecoat comprises a film-forming water-insoluble polymer selected from the group consisting of cellulosic polymers, polyurethanes, polyacryls, polymethacryls, polysiloxanes, and mixtures thereof; and
 (b) the topcoat comprises a film-forming water-insoluble polymer selected from the group consisting of polyurethanes, polyacryls, polymethacryls, polystyrene-polyacryl mixtures, styrene-acryl copolymers, siloxane-urethane copolymers, cellulosic polymers, polyesters, polyurethane-polymethacryl mixtures, silicone-acryl copolymers, vinyl acetate polymers, and mixtures thereof.

5. A film according to claim 2 further comprising a midcoat wherein the midcoat comprises a film-forming water-insoluble polymer selected from the group consisting of cellulosic polymers, polyurethanes, polyacryls, polymethacryls, polysiloxanes, and mixtures thereof.

6. A film according to claim 1 wherein the Tip Wear Index is less than about 0.70.

7. A film according to claim 1 wherein the Tip Wear Index is less than about 0.65.

8. A kit suitable for use as a nail polish for mammalian nails, the kit comprising two or more different compositions wherein each composition comprises a film-forming polymer and a carrier, wherein the compositions when applied to the nail form a film exhibiting a Tip Wear Index of less than about 0.80.

9. A kit according to claim 8 wherein the polymer is selected from the group consisting of polyurethanes, polyacryls, polymethacryls, cellulosic polymers, styrene-acryl copolymers, polystyrene-polyacryl mixtures, polysiloxanes, polyesters, urethane-acryl copolymers, siloxane-urethane copolymers, polyurethane-polymethacryl mixtures, silicone-acryl copolymers, vinyl acetate polymers, and mixtures thereof.

10. A kit according to claim 9 wherein one or more of the compositions comprises a water-insoluble film-forming polymer selected from the group consisting of polyurethanes, polyacryls, polymethacryls, urethane-acryl copolymers, styrene-acryl copolymers, and mixtures thereof.

11. A kit according to claim 10 wherein one or more of the compositions comprises a water-insoluble film-forming polyurethane.

12. A kit according to claim 9 wherein one or more of the compositions comprises a water-insoluble film-forming polymer selected from the group consisting of polyurethanes, polyacryls, polymethacryls, polystyrene-polyacryl mixtures, styrene-acryl copolymers, siloxane-urethane copolymers, cellulosic polymers, polyesters, polyurethane-polymethacryl mixtures, silicone-acryl copolymers, vinyl acetate polymers, and mixtures thereof.

13. A kit according to claim 12 wherein the water-insoluble film-forming polymer of one of the compositions is a cross-linked polymer.

14. A kit according to claim 9 comprising a basecoat composition and a topcoat composition wherein:
   (a) the basecoat composition comprises a film-forming water-insoluble polymer selected from the group consisting of polyurethanes, polyacryls, polymethacryls, urethane-acryl copolymers, styrene-acryl copolymers, and mixtures thereof; and
   (b) the topcoat composition comprises a film-forming water-insoluble polymer selected from the group consisting of polyurethanes, polyacryls, polymethacryls, polystyrene-polyacryl mixtures, styrene-acryl copolymers, siloxane-urethane copolymers, cellulosic polymers, polyesters, polyurethane-polymethacryl mixtures, silicone-acryl copolymers, vinyl acetate polymers, and mixtures thereof.

15. A kit according to claim 9 comprising a basecoat composition and a topcoat composition wherein:
   (a) the basecoat composition comprises a film-forming water-insoluble polymer selected from the group consisting of polyurethanes, polyacryls, polymethacryls, urethane-acryl copolymers, styrene-acryl copolymers, and mixtures thereof; and
   (b) the topcoat composition comprises a film-forming water-insoluble polymer selected from the group consisting of cellulosic polymers, polyurethanes, polyacryls, polymethacryls, polysiloxanes, and mixtures thereof.

16. A kit according to claim 9 comprising a basecoat composition and a topcoat composition wherein:
   (a) the basecoat composition comprises a film-forming water-insoluble polymer selected from the group consisting of cellulosic polymers, polyurethanes, polyacryls, polymethacryls, polysiloxanes, and mixtures thereof; and
   (b) the topcoat composition comprises a film-forming water-insoluble polymer selected from the group consisting of polyurethanes, polyacryls, polymethacryls, polystyrene-polyacryl mixtures, styrene-acryl copolymers, siloxane-urethane copolymers, cellulosic polymers, polyesters, polyurethane-polymethacryl mixtures, silicone-acryl copolymers, vinyl acetate polymers, and mixtures thereof.

17. A kit according to claim 14 further comprising a midcoat composition comprising a film-forming water-insoluble polymer selected from the group consisting of cellulosic polymers, polyurethanes, polyacryls, polymethacryls, polysiloxanes, and mixtures thereof.

18. A kit according to claim 8 wherein the Tip Wear Index is less than about 0.70.

19. A kit according to claim 8 wherein the Tip Wear Index is less than about 0.65.

20. A kit according to claim 8 further comprising information that use of the kit provides one or more long wear benefits.

21. A method of coating mammalian nails with a nail polish film, the film comprising two or more different layers, wherein the method comprises the steps of:
   (i) applying a basecoat composition contiguously to the nail, wherein the basecoat composition comprises a film-forming polymer and a liquid diluent;
   (ii) removing sufficient liquid diluent from the basecoat composition to form a substantially dry basecoat;
   (iii) applying a topcoat composition to the nail, wherein the topcoat composition comprises a film-forming polymer and a liquid diluent; and
   (iv) removing sufficient liquid diluent from the topcoat composition to form a substantially dry topcoat;
   wherein the film exhibits a Tip Wear Index of less than about 0.80.

22. A nail polish film comprising two or more different layers wherein each layer comprises a film-forming polymer, wherein the film exhibits a Jagged Index of less than about 0.85.

23. A film according to claim 22 comprising a basecoat and a topcoat wherein:
   (a) the basecoat comprises a film-forming water-insoluble polymer selected from the group consisting of polyurethanes, polyacryls, polymethacryls, urethane-acryl copolymers, styrene-acryl copolymers, and mixtures thereof; and
   (b) the topcoat comprises a film-forming water-insoluble polymer selected from the group consisting of polyurethanes, polyacryls, polymethacryls, polystyrene-polyacryl mixtures, styrene-acryl copolymers, siloxane-urethane copolymers, cellulosic polymers, polyesters, polyurethane-polymethacryl mixtures, silicone-acryl copolymers, vinyl acetate polymers, and mixtures thereof.

24. A film according to claim 22 comprising a basecoat and a topcoat wherein:
   (a) the basecoat comprises a film-forming water-insoluble polymer selected from the group consisting of polyurethanes, polyacryls, polymethacryls, urethane-acryl copolymers, styrene-acryl copolymers, and mixtures thereof; and
   (b) the topcoat comprises a film-forming water-insoluble polymer selected from the group consisting of cellulosic polymers, polyurethanes, polyacryls, polymethacryls, polysiloxanes, and mixtures thereof.

25. A film according to claim 22 comprising a basecoat and a topcoat wherein:
   (a) the basecoat comprises a film-forming water-insoluble polymer selected from the group consisting of cellulosic polymers, polyurethanes, polyacryls, polymethacryls, polysiloxanes, and mixtures thereof; and
   (b) the topcoat comprises a film-forming water-insoluble polymer selected from the group consisting of polyurethanes, polyacryls, polymethacryls, polystyrene-polyacryl mixtures, styrene-acryl copolymers, siloxane-urethane copolymers, cellulosic polymers, polyesters, polyurethane-polymethacryl mixtures, silicone-acryl copolymers, vinyl acetate polymers, and mixtures thereof.

26. A film according to claim 23 further comprising a midcoat wherein the midcoat comprises a film-forming water-insoluble polymer selected from the group consisting of cellulosic polymers, polyurethanes, polyacryls, polymethacryls, polysiloxanes, and mixtures thereof.

27. A film according to claim 22 wherein the Jagged Index is less than about 0.80.

28. A kit suitable for use as a nail polish for mammalian nails, the kit comprising two or more different compositions wherein each composition comprises a film-forming polymer and a carrier, wherein the compositions when applied to the nail form a film exhibiting a Jagged Index of less than about 0.85.

29. A kit according to claim 28 wherein the polymer is selected from the group consisting of polyurethanes, polyacryls, polymethacryls, cellulosic polymers, styrene-acryl copolymers, polystyrene-polyacryl mixtures, polysiloxanes, polyesters, urethane-acryl copolymers, siloxane-urethane copolymers, polyurethane-polymethacryl mixtures, silicone-acryl copolymers, vinyl acetate polymers, and mixtures thereof.

30. A kit according to claim 29 wherein one or more of the compositions comprises a water-insoluble film-forming polymer selected from the group consisting of polyurethanes, polyacryls, polymethacryls, urethane-acryl copolymers, styrene-acryl copolymers, and mixtures thereof.

31. A kit according to claim 30 wherein one or more of the compositions comprises a water-insoluble film-forming polyurethane.

32. A kit according to claim 29 wherein one or more of the compositions comprises a water-insoluble film-forming polymer selected from the group consisting of polyurethanes, polyacryls, polymethacryls, polystyrene-polyacryl mixtures, styrene-acryl copolymers, siloxane-urethane copolymers, cellulosic polymers, polyesters, polyurethane-polymethacryl mixtures, silicone-acryl copolymers, vinyl acetate polymers, and mixtures thereof.

33. A kit according to claim 32 wherein the water-insoluble film-forming polymer of one of the compositions is a cross-linked polymer.

34. A kit according to claim 29 comprising a basecoat composition and a topcoat composition wherein:
  (a) the basecoat composition comprises a film-forming water-insoluble polymer selected from the group consisting of polyurethanes, polyacryls, polymethacryls, urethane-acryl copolymers, styrene-acryl copolymers, and mixtures thereof; and
  (b) the topcoat composition comprises a film-forming water-insoluble polymer selected from the group consisting of polyurethanes, polyacryls, polymethacryls, polystyrene-polyacryl mixtures, styrene-acryl copolymers, siloxane-urethane copolymers, cellulosic polymers, polyesters, polyurethane-polymethacryl mixtures, silicone-acryl copolymers, vinyl acetate polymers, and mixtures thereof.

35. A kit according to claim 29 comprising a basecoat composition and a topcoat composition wherein:
  (a) the basecoat composition comprises a film-forming water-insoluble polymer selected from the group consisting of polyurethanes, polyacryls, polymethacryls, urethane-acryl copolymers, styrene-acryl copolymers, and mixtures thereof; and
  (b) the topcoat composition comprises a film-forming water-insoluble polymer selected from the group consisting of cellulosic polymers, polyurethanes, polyacryls, polymethacryls, polysiloxanes, and mixtures thereof.

36. A kit according to claim 29 comprising a basecoat composition and a topcoat composition wherein:
  (a) the basecoat composition comprises a film-forming water-insoluble polymer selected from the group consisting of cellulosic polymers, polyurethanes, polyacryls, polymethacryls, polysiloxanes, and mixtures thereof; and
  (b) the topcoat composition comprises a film-forming water-insoluble polymer selected from the group consisting of polyurethanes, polyacryls, polymethacryls, polystyrene-polyacryl mixtures, styrene-acryl copolymers, siloxane-urethane copolymers, cellulosic polymers, polyesters, polyurethane-polymethacryl mixtures, silicone-acryl copolymers, vinyl acetate polymers, and mixtures thereof.

37. A kit according to claim 34 further comprising a midcoat composition comprising a film-forming water-insoluble polymer selected from the group consisting of cellulosic polymers, polyurethanes, polyacryls, polymethacryls, polysiloxanes, and mixtures thereof.

38. A kit according to claim 28 wherein the Jagged Index is less than about 0.80.

39. A kit according to claim 28 further comprising information that use of the kit provides one or more long wear benefits.

40. A method of coating mammalian nails with a nail polish film, the film comprising two or more different layers, wherein the method comprises the steps of:
  (i) applying a basecoat composition contiguously to the nail, wherein the basecoat composition comprises a film-forming polymer and a liquid diluent;
  (ii) removing sufficient liquid diluent from the basecoat composition to form a substantially dry basecoat;
  (iii) applying a topcoat composition to the nail, wherein the topcoat composition comprises a film-forming polymer and a liquid diluent; and
  (iv) removing sufficient liquid diluent from the topcoat composition to form a substantially dry topcoat;
wherein the film exhibits a Jagged Index of less than about 2.85.

41. A nail polish film comprising two or more different layers wherein each layer comprises a film-forming polymer, wherein the film exhibits a Total Wear Index of less than about 0.80.

42. A kit suitable for use as a nail polish for mammalian nails, the kit comprising two or more different compositions wherein each composition comprises a film-forming polymer and a carrier, wherein the compositions when applied to the nail form a film exhibiting a Total Wear Index of less than about 0.80.

* * * * *

UNITED STATES PATENT AND TRADEMARK OFFICE
CERTIFICATE OF CORRECTION

PATENT NO. : 6,080,414
DATED : June 27, 2000
INVENTOR(S) : E. D. Smith et al.

It is certified that error appears in the above-identified patent and that said Letters Patent is hereby corrected as shown below:

Column 1,
Line 38,, "See." should read --See,--.
Line 43, "see." should read --See,--.
Line 43, "WP" should read --JP--.

Column 2,
Line 46, "usefull" should read --useful--.

Column 7,
Line 50, "$T_8$" should read --$T_g$--.

Column 8,
Line 41, "$10^{+01}$" should read --$10^{-01}$--.
Line 56, "$T_8$" should read --$T_g$--.

Column 11,
Line 27, "13%." should read 13%,--.
Line 38, "$(T_8)$" should read --$(T_g)$--.

Column 12,
Line 2, "ioalkyl" should read --alkyl--.

Column 13,
Line 1, "Quaternium-15®" should read --Quaternium-15®--.

Column 14,
Line 29, "Bentonel" should read --Bentone®--.

Column 22,
Line 44, "l" should read --1--.

UNITED STATES PATENT AND TRADEMARK OFFICE
CERTIFICATE OF CORRECTION

PATENT NO. : 6,080,414
DATED : June 27, 2000
INVENTOR(S) : E. D. Smith et al.

It is certified that error appears in the above-identified patent and that said Letters Patent is hereby corrected as shown below:

Column 23,
Line 50, "the" should read --and the--.
Line 59, "layers" should read ferent layers--.
Line 62, "0.90" should read --0.80--.

Column 28,
Line 44, "2.85" should read --0.85--.

Signed and Sealed this

Nineteenth Day of June, 2001

*Attest:*

NICHOLAS P. GODICI
*Attesting Officer*     *Acting Director of the United States Patent and Trademark Office*